United States Patent [19]

Harris

[11] Patent Number: 4,660,229

[45] Date of Patent: Apr. 28, 1987

[54] WATER-TIGHT EAR ENCLOSURE

[76] Inventor: Paul W. Harris, 1130 Lowe Ave., Adrian, Mich. 49221

[21] Appl. No.: 808,794

[22] Filed: Dec. 13, 1985

[51] Int. Cl.<sup>4</sup> ............................................... A42B 1/06
[52] U.S. Cl. .......................................... 2/209; 2/174; 2/243 R; 128/151
[58] Field of Search ........................ 2/174, 209, 243 R; 128/151

[56] References Cited

U.S. PATENT DOCUMENTS

| | | | |
|---|---|---|---|
| 1,255,800 | 2/1918 | Schurmier | 2/174 |
| 2,763,869 | 9/1956 | Bogart et al. | 2/174 |
| 2,812,517 | 11/1957 | Bogart | 2/174 |
| 3,003,514 | 2/1967 | Wessels | 2/174 |
| 3,525,103 | 8/1970 | Yonan | 2/174 |
| 3,823,713 | 7/1974 | Shah | 2/174 |
| 3,841,325 | 10/1974 | Pickard | 2/174 |
| 4,036,235 | 7/1977 | Hathaway | 128/151 |
| 4,134,153 | 1/1979 | Voorhees | 2/174 |
| 4,308,623 | 1/1982 | Voorhees | 2/174 |

Primary Examiner—Werner H. Schroeder
Assistant Examiner—Mary A. Ellis
Attorney, Agent, or Firm—Cullen, Sloman, Cantor, Grauer, Scott & Rutherford

[57] ABSTRACT

A water-tight ear enclosure having a water-impervious membrane secured to a flexible, inelastic strip about a portion of an opening in the membrane and an elastic strip secured to opposite ends of the flexible, inelastic strip and to the remaining portions of the opening in the membrane. The strip is formed of a thin, polymeric material in a J shape which is adapted to be received in front of the tragus of the ear and below and behind the lobule of the ear. The elastic strip is adapted to extend around the back of the external ear and in one embodiment includes an extension extending below the ear to form a secondary seal. The flexible, inelastic strip includes an adhesive for attaching the strip to the skin of a person adjacent the ear. The membrane is a flexible plastic film. The seal is established by the combination of the adhesively secured plastic strip and the inward biasing force of the elastic strip bearing upon the back of the external ear.

14 Claims, 4 Drawing Figures

WATER-TIGHT EAR ENCLOSURE

BACKGROUND OF THE INVENTION

I. Technical Field

The present invention relates to ear enclosures. More particularly, the invention relates to externally secured ear enclosures which establish a seal about the external ear.

II. Brief Description of the Background Art

Various types of ear protection devices have been developed which inhibit or prevent foreign material from entering the ear canal. Persons who are susceptible to ear infections or contracting "swimmer's ear" are recommended to use ear protection devices when swimming. Internal ear protection devices such as ear plugs are objectionable because they are uncomfortable to some persons and may be inappropriate if the ear canal is inflamed. Ear plugs may themselves become an irritant and may aggravate an ear infection. Further, ear plugs reduce or eliminate the ability of the wearer to hear, making ear plugs dangerous, especially for children.

Following ear surgery, it is generally recommended to protect the ear during the healing process. Internal ear protection devices are objectionable in some instances, especially when the surgical procedure involves the ear canal.

External ear protection devices are disclosed in the prior art and include cup-shaped enclosures having an adhesive perimeter which is adhered to the head of a user. Such devices are ineffective, particularly when submerged due to the difficulty of establishing and maintaining a seal as a result of hair behind the ear and the relative rigidity of the cup-shaped ear enclosure. Also, such structures are relatively expensive and generally intended for repeated use and tend to become less effective with each successive usage due to a loss of adhesion.

Disposable external ear protection devices are also disclosed in the prior art and generally comprise bag-like devices having an opening for receiving the external ear. An adhesive is applied to the perimeter of the opening which is intended to secure the device to the head of the wearer. The adhesive may be applied directly to the bag-like device or applied to a supporting member which is in turn attached to the bag membrane. Examples of such bag-like devices are disclosed by Vorhees in U.S. Pat. No. 4,134,153, issued Jan. 16, 1979, and No. 4,308,623, issued Jan. 5, 1982, both of which provide a plastic enclosure for the external ear having an opening in which the outer ear is received. The opening is surrounded by an adhesive for attaching the enclosure to the ear and establishing a seal.

A primary problem with a purely adhesive attachment and sealing device is that considerable care is required in installing the device to establish a good seal. The seal may be interfered with by hair generally located above and behind the ear. If the degree of adhesiveness is increased to overcome interference caused by hair or other foreign substances such as body oils, the device may become difficult to remove, causing discomfort as a result of pulling hair and skin. If the device is secured solely by adhesive, a significant danger exists that the device may become dislodged by accidental application of external force on the device.

Adhesively secured, external, bag-like devices are not well-suited for use by persons who also wear glasses since the adhesive securing the device to the wearer's head above the ear prevents the end pieces of the skull temples from properly seating on top of the ear.

Another problem with entirely adhesively secured external bag-like devices is that air trapped within the device cannot be easily removed, especially after the device becomes wet since water between the skin and adhesive will interfere with resealing the device.

The present invention is directed to overcoming one or more of the problems as set forth above.

SUMMARY OF THE INVENTION

In one aspect of the present invention, a water-tight enclosure for an ear is provided which features a membrane which is substantially impervious to water that is gathered to form an opening for receiving a wearer's ear. A portion of the perimeter of the opening is secured to a flexible, inelastic strip having an adhesive surface for adhesively attaching a portion of the perimeter of the opening to the skin in front of the tragus of the ear. The remaining portion of the perimeter of the opening is secured to an elastic string or other means for elastically biasing the remainder of the opening into sealing engagement with the ear.

In another aspect of the present invention, the flexible inelastic strip may be J-shaped and thereby adapted to be secured in front of the tragus and extending partially below and behind the ear lobule portion. In this way, the areas about the ear which have the least quantity of hair and therefore least likelihood of interference with the adhesive sealing caused by hair are spanned by the adhesive while the other portions of the ear are sealed by the action of the elastic strip.

A still further aspect of the present invention is the provision of a secondary seal along the base of the external ear by extending the elastic strip from the short leg of the J-shaped member across the base of the J-shaped member to a point intermediate the two ends of the J-shaped strip and securing the membrane to the adhesive-coated strip and the elastic strip at the base of the ear where seal failure caused by subcutaneous movement of the jaw bone can cause failure of the adhesive to bond to the skin.

It will be readily appreciated that the enclosure does not rely exclusively upon an adhesive means for securing the enclosure to the head of a wearer but instead utilizes the combination of an adhesive to establish a seal at the front of the external ear and an elastic member which establishes the seal by contracting about the ear so as to form a seal. The enclosure is simple to install and remove and is not interfered with by hair above and behind the ear. The enclosure of the present invention does not interfere with the wearing of glasses since the elastic member seats itself in the crease at the top of the ear and does not rely upon an adhesive member adhering to the skull above the ear and spanning the top of the ear by the membrane.

Another advantage of the present invention is that air within the membrane after installation may be purged by forcing entrapped air to pass under the elastic strip. This may be accomplished even if the apparatus is wet without harming the seal. Since the elastic portion grips the ear, the connection does not rely solely upon adhesive and is more resistant to accidental removal.

A still further advantage of the ear enclosure of this invention is that it does not inhibit the hearing of the wearer, making it particularly useful for children.

The above objects, features and advantages of the present invention will become apparent upon review of the following detailed description of the illustrated embodiment in the attached drawings and in view of the appended claims.

DETAILED DESCRIPTION OF THE INVENTION

Figure 1:
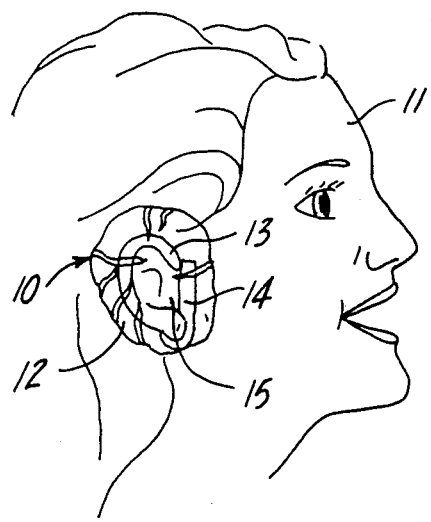
FIG. 1 is a side elevational view of the illustrated embodiment of the water-tight enclosure for an ear of the present invention shown secured to the ear of a person.
Figure 2:
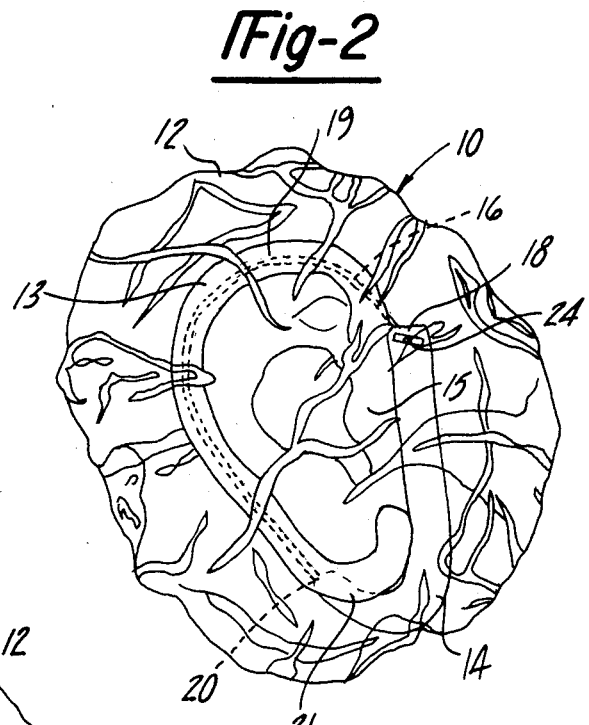
FIG. 2 is a side elevational view of the illustrated embodiment of the present invention shown secured to the ear of a person and showing the portion of the J-shaped strip located behind the ear in phantom lines.

Referring now to FIGS. 1 and 2 of the drawings, the ear enclosure 10 is shown secured to the head 11 of a wearer. The ear enclosure 10 includes a membrane 12 for enclosing the external ear 13. The membrane 12 is preferably clear polyethylene film but may alternatively be another substantially impermeable material which may be tinted or colored as desired. The membrane 12 is secured to a strip 14 of flexible, inelastic material which is adapted to be secured to the head 11 in front of the tragus 15 portion of the ear. The strip 14 is an elongate member which extends vertically from the upper portion of the ear to the lower portion of the ear in front of the tragus 15. The strip 14 is preferably J-shaped but may be made in several differently configured elongate shapes. Opposite ends of the strip 14 are interconnected by an elastic strip, or rubber band, formed of an elastomeric material. The elastic strip 16 is secured along its length to the membrane 12. The strip 14 and elastic strip 16 form a continuous loop which encompasses an opening 17 in the membrane 12. The opening 17 is defined by a continuous edge of the membrane 12.

The strip 14, as shown in the illustrated embodiment, is a J-shaped member having a first end 18 at the terminal end of the long leg of the J shape. The first end 18 is adapted to be secured to the head just below and adjacent to the helix 19 of the ear. The second end 20 of the strip 14 is located at the terminal end of the short leg of the J shape. The second end 20 is adapted to be secured to the head behind the ear so that the short leg of the J passes behind the lobule 21 of the ear. The strip 14 includes means 22 for adhesively attaching the strip to the wearer's head. The strip 14 may be either coated with an adhesive 22 on the side of the strip placed in contact with the skin or it may be provided by attaching adhesive tape 22 to the side opposite the side adapted to contact the person's skin with a portion of the tape extending over the edge of the strip 14. If desired, both an adhesive coating 22 and tape 22 may be provided on the J-shaped member.

The strip 14 includes two or more holes 23 with one of said holes being located in the first end 18 and another of said holes being located in the second end 20. Opposite ends of the elastic strip 16 are attached to clips 24 that anchor the elastic strip 16 to the strip 14. In an alternative embodiment shown in FIG. 3, the elastic strip 16 includes an extension 26 which extends from the second end to an intermediate point on the J-shaped member between the first and second ends. The extension 26 provides a secondary seal which augments the primary seal at the lower portion of the enclosure formed by the adhesive coating 22 on the lower part of the strip 14.

Figure 3:
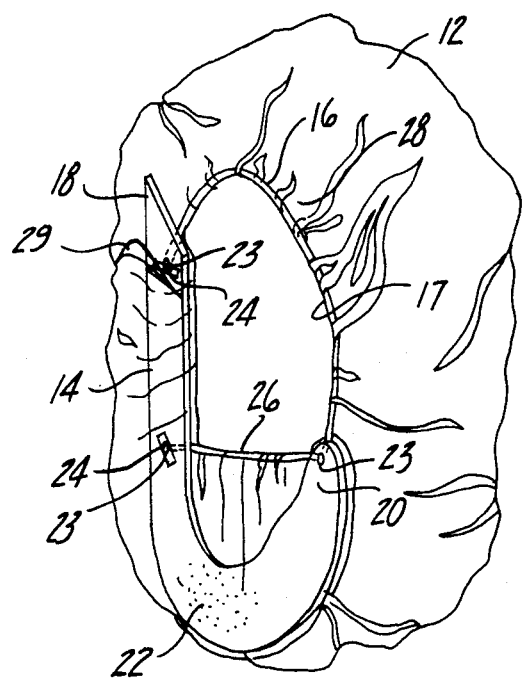
FIG. 3 is a perspective view of an alternative illustrated embodiment of the present invention, having a secondary elastic sealing means below the ear.

In the illustrated embodiment, as best shown in FIG. 3, the elastic strip 16 and J-strip 14 are attached to the membrane 12 by a hem 28 which comprises a reversely turned portion of the membrane 12 which encircles the J strip 14 and elastic strip 16 and is secured back on the membrane 12 by a heat seal or molding process. A protective cover 29 may be provided to protect the adhesive layer 22 until the apparatus is to be used. The protective cover may include a thumb tab for aiding in separation of the cover from the adhesive layer.

Figure 4:
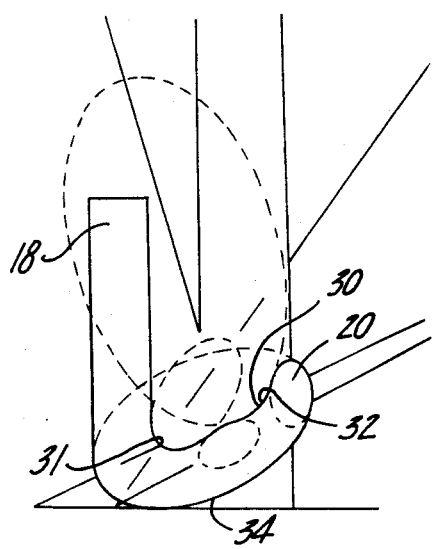
FIG. 4 is a plan view of the J-shaped strip shown in the illustrated embodiment of the present invention.

Referring now to FIG. 4, the J-shaped strip 14 is shown separate from the ear enclosure apparatus to more clearly show the preferred shape of the J-shaped strip 14. The J-shaped strip 14 includes a sculpted edge 30 having a lobule cutout 31 at the intersection of the two legs of the J-shaped strip and a concha cutout 32 located between the lobule cutout and the second end which is adapted to provide clearance between the concha portion of the external ear and the J-shaped strip 14. A raised edge 34 is provided on the opposite edge of the short leg of the J-shaped strip.

The ear enclosure 10 is easily applied by stretching the elastic strip 16 over the external ear 13. The elastic strip 16 is biased inwardly and automatically seats itself within the crease formed between the head 11 and the back of the external ear 13. The protective cover 29 is then removed from the adhesive layer 22 and strip 14 is pressed against the skin in front of the tragus 15 and behind the lobule 21, causing the pressure sensitive adhesive layer 22 to firmly adhere to the skin, thereby forming a seal therewith. It will be appreciated that the elastic strip 16 in combination with the adhesive of the strip 14 combine to form a seal without the necessity of providing a complete ring of adhesive. The elastic strip 16 can establish a seal regardless of the presence of hair above and behind the ear.

The invention also provides a convenient method of releasing air from the inside of the membrane without interfering with the adhesive portion of the seal. When swimming, air in the ear enclosure tends to cause the membrane 12 to form a bubble. The air may be released by breaking the seal between the elastic strip 16 and the ear and then reseating the elastic strip 16. Purging air from the enclosure could not conveniently be achieved in prior art all-adhesive ear enclosures since any moisture on the surface of the skin to which the adhesive is applied would prevent reestablishing the adhesive seal.

Unlike prior art ear plugs, the present invention does not significantly impair a wearer's hearing when in use. Sounds can be heard through the membrane 12, which is particularly important when the apparatus is used by children when swimming who should be able to hear instructions from lifeguards, instructors or others for safety.

Assembly of the ear enclosure apparatus 10 may be accomplished by cutting a substantially circular blank from a polyethylene film to form the membrane 12. The strip 14 would preferably be cut from a 7 to 20 mil. polypropylene sheet substantially in accordance with the shape shown in FIG. 4 and coated with an acrylic adhesive to which a protective paper is applied. The strip 14 would then be cut to shape and drilled to receive the elastic strip 16. Elastic strip 16 would then be assembled to the strip 14 and mechanically fastened to the tab by clips 24 or possibly a heat sealing operation. The strip 14 and elastic strip 16 would then be married to the membrane, or blank of polyethylene film by drawing the perimeter of the blank around the strip 14 and elastic strip 16 assembly and doubling it back upon itself prior to heat sealing.

The above description of embodiments of a new and improved water-tight ear enclosure is intended by way of example and not by way of limitation. It will be appreciated that the structure, materials and method making the ear enclosure may be modified without departing from the spirit and scope of the invention. The scope of the invention is to be determined based upon the full scope of the following claims and all equivalents thereof.

I claim:

1. A water-tight ear enclosure for enclosing and sealing a person's ear, comprising:
   (a) a water-impervious membrane gathered around an opening forming a bag-shaped enclosure defined by a continuous edge of said membrane;
   (b) a flexible inelastic strip secured along a first portion of said impervious membrane edge;
   (c) an elastic flexible element secured along a second portion of said impervious membrane edge connected at its opposed ends to said flexible inelastic strip, drawing said membrane tightly around the back of the ear lobe; and
   (d) adhesive means on said flexible inelastic strip releasably attaching said strip to said person's head across the tragus of the ear.

2. The water-tight enclosure of claim 1 wherein said flexible inelastic strip is J-shaped with one end being disposed at the terminal end of the longer leg of the J-shape and being adapted to be received adjacent the upper portion of the helix of the ear and another end being disposed at the terminal end of the shorter leg of the J shape being adapted to be received behind the lobule portion of the ear and said elastic element attached at its opposed ends to the ends of said J-shaped inelastic strip.

3. The water-tight ear enclosure defined in claim 1, characterized in that said ear enclosure includes a second elastic element connected at one end to a mid portion of said longer leg of said J-shaped inelastic strip and the opposite end of said second elastic element connected to the end of said shorter leg of said inelastic element and said second elastic element secured along a third portion of said membrane edge.

4. The water-tight enclosure of claim 1 wherein said continuous edge of said membrane is formed by reversely turning a peripheral edge of said membrane about the first and second means and securing said peripheral edge to a radially inwardly disposed portion of said membrane whereby a hem is formed which encloses the first and second means.

5. The water-tight enclosure of claim 1 wherein said flexible, inelastic strip comprises a thin plate having adhesive applied to one side thereof.

6. The water-tight enclosure of claim 1 wherein said strip comprises a thin plate to which tape is partially attached to the side opposite the person's head.

7. A water-tight enclosure for an ear comprising:
   an elongate, flexible inelastic strip having first and second ends, said strip being adapted to be secured to the area of the head in front of and approximate to the tragus with said strip spanning the basal portion of the tragus, said strip having a pressure-sensitive adhesive one side thereof;
   an elastic strip interconnecting said first and second ends of said strip, said elastic strip being adapted to encircle the external ear proximate the head with an inwardly biasing force; and
   a substantially water-impervious membrane secured to said strip and said elastic strip, wherein an opening is defined having a perimeter which is secured to said strip and said elastic strip, said opening being adapted to receive the ear wherein an enclosure is formed by the membrane over the ear and a seal is established at the perimeter of the opening.

8. The water-tight enclosure of claim 5 wherein said inelastic strip is J-shaped with said first end being disposed at the terminal end of the longer leg of the J shape and being adapted to be received adjacent the upper portion of the helix of the ear and said second end being disposed at the terminal end of the shorter leg of the J shape being adapted to be received behind the lobule portion of the ear.

9. The water-tight enclosure of claim 8 wherein said elastic strip extends from said first end and through an opening in said second end to an intermediate point on the J-shaped member between said first and second ends.

10. The water-tight enclosure of claim 7 wherein the continuous edge of said membrane is formed by reversely turning a peripheral edge of said membrane about the inelastic strip and the elastic strip and securing said peripheral edge to a radially inwardly disposed portion of said membrane whereby a hem is formed which encloses said inelastic strip and said elastic strip.

11. The water-tight enclosure of claim 7 wherein said flexible, inelastic strip comprises a thin plate having adhesive applied to one side thereof.

12. The water-tight enclosure of claim 7 wherein said strip comprises a thin plate to which tape is partially attached to the side opposite the person's head.

13. A water-tight ear enclosure for enclosing and sealing a person's ear, comprising:
   (a) a water-impervious membrane gathered along an opening forming a bag-shaped enclosure defined by a continuous edge of said membrane;
   (b) a J-shaped flexible inelastic strip attached to a first portion of said membrane edge with said membrane edge extending along the longer leg of said J-shaped strip adapted to be received adjacent the upper portion of the helix of the ear;
   (c) an elastic flexible element secured along a second portion of said membrane edge connected at its opposite ends to the ends of said J-shaped flexible inelastic strip, drawing said membrane tightly around the back of the ear lobe; and
   (d) adhesive means on said inelastic strip releasably attaching said strip to said person's head, across the tragus of the ear and cheek.

14. The water-tight ear enclosure defined in claim 13, characterized in that said enclosure includes a second elastic element connected at one end to a mid portion of said longer leg of said J-shaped inelastic strip and the opposed end connected to the end of the shorter leg of said inelastic strip, and said second elastic element retained along a third portion of said continuous membrane edge.

* * * * *